United States Patent
Cho et al.

(10) Patent No.: US 10,610,515 B2
(45) Date of Patent: Apr. 7, 2020

(54) COMPOSITION INCLUDING INDOPROFEN AND USE THEREOF

(71) Applicants: Samsung Electronics Co., Ltd., Suwon-si, Gyeonggi-do (KR); Research & Business Foundation Sungkyunkwan University, Suwon-si, Gyeonggi-do (KR)

(72) Inventors: Sungchun Cho, Hwaseong-si (KR); Jongsun Kang, Suwon-si (KR); Sangchul Park, Seongnam-si (KR); Yunil Lee, Yongin-si (KR); Hyebeen Kim, Suwon-si (KR); Hyeyoung Lee, Suwon-si (KR)

(73) Assignees: SAMSUNG ELECTRONICS CO., LTD., Suwon-si (KR); RESEARCH & BUSINESS FOUNDATION, SUNGKYUNKWAN UNIVERSITY, Suwon-si (KR)

( * ) Notice: Subject to any disclaimer, the term of this patent is extended or adjusted under 35 U.S.C. 154(b) by 8 days.

(21) Appl. No.: 15/284,267

(22) Filed: Oct. 3, 2016

(65) Prior Publication Data
US 2017/0095451 A1    Apr. 6, 2017

(30) Foreign Application Priority Data
Oct. 1, 2015    (KR) ........................ 10-2015-0138617

(51) Int. Cl.
*A61K 31/4035*    (2006.01)

(52) U.S. Cl.
CPC ............................... *A61K 31/4035* (2013.01)

(58) Field of Classification Search
None
See application file for complete search history.

(56) References Cited

U.S. PATENT DOCUMENTS

| | | |
|---|---|---|
| 2006/0035849 A1 | 2/2006 | Spiegelman et al. |
| 2012/0183600 A1 | 7/2012 | Chen |
| 2016/0089340 A1 | 3/2016 | Cho et al. |

FOREIGN PATENT DOCUMENTS

| | | | |
|---|---|---|---|
| KR | 2016-0037753 A | | 4/2016 |
| WO | WO2005/049014 | * | 6/2005 |
| WO | WO 2006/050451 | * | 5/2006 |
| WO | WO 2006-050451 A2 | | 5/2006 |
| WO | WO 2010/019549 A2 | | 2/2010 |

OTHER PUBLICATIONS

Pedrazzi et al. in European Journal of Rheumatology and Inflammation 4(1): 26-31 (1981).*
Rieu et al. in Journal of Physiology 5483-5492 (2009).*
Huskisson et al. in European Journal of Rheumatology and Inflammation 4(1): 97-102 (1981) (Abstract).*
Handschin et al. in Nature 454(7203): 463-469 (2008). (Year: 2008).*
Brooks et al. in Pharmacy and Pharmacology 55: 519-526 (2003) (Year: 2003).*
Brooks et al. in Journal of Pharmacy and Pharmacology 65, 519-526 (2003) (Year: 2003).*
Stygles et al. in Res Commun Chem Pathol Pharmacol. 18(2):329-40 (1977) (Year: 1977).*
Castillo-Quan in Disease Models and Mechanisms 5, 293-295 (2012) (Year: 2012).*
Arany et al., "HIF-independent regulation of VEGF and angiogenesis by the transcriptional coactivator PGC-1α", *Nature* 451:1008-1012 (2008).
Arany, et al., "Gene expression-based screening identifies microtubule inhibitors as inducers of PGC-1α and oxidative phosphorylation", *PNAS (Proceedings of the National Academy of Sciences)*, 105(12): 4721-4726 (2008).
Baar, et al., "Adaptations of skeletal muscle to exercise: rapid increase in the transcriptional coactivator PGC-1", *FASEB Journal*, 16(14):1879-1886 (2002).
Handschin, et al., "PGC-1α regulates the neuromuscular junction program and ameliorates Duchenne muscular dystrophy", *Genes & Development*, 21:770-783 (2007).
Lin, et al., "Defects in Adaptive Energy Metabolism with CNS-Linked Hyperactivity in PGC-1α Null Mice", *Cell*, 119:121-135 (2004).
Lunn et al., "Indoprofen Upregulates the Survival Motor Neuron Protein through a Cyclooxygenase-Independent Mechanism", *Chemistry & Biology*, 11(11): 1489-1493 (2004).
Sandri et al., "PGC-1α protects skeletal muscle from atrophy by suppressing FoxO3 action and atrophy-specific gene transcription", *PNAS (Proceedings of the National Academy of Sciences)*, 103(44):16260-16265 (2006).
Zhang et al., "Novel Small-Molecule PGC-1α Transcriptional Regulator With Beneficial Effects on Diabetic db/db Mice", *Diabetes*, 62(4):1297-1307 (2013).
Frazin, Natalie "Pain Reliever May Provide Clues for Treating Spinal Muscular Atrophy," *National Institute of Neurological Disorders and Stroke, Press Release* Mar. 3, 2005.
Kleiner, et al., "PPARδ Agonism Activates Fatty Acid Oxidation via PGC-1α but Does Not Increase Mitochondrial Gene Expression and Function", *The Journal of Biological Chemistry*, 284(28): 18624-18633 (2009).
Narkar et al., "AMPK and PPARδ agonists are exercise mimetics", *Cell*, 134(3):405-415 (2008).
Tanaka et al., "Activation of peroxisome proliferator-activated receptor δ induces fatty acid β-oxidation in skeletal muscle and attenuates metabolic syndrome", Proc. Natl. Acad. Sci. USA, 100(26): 15924-15929 (2003).
Woldt et al., "Rev-erb- α modulates skeletal muscle oxidative capacity by regulating mitochondrial biogenesis and autophagy", *Nat. Med.*, 19(8):1039-1046 (2013).
Bravard et al "FTO Is Increased in Muscle During Type 2 Diabetes, and Its Overexpression in Myotubes Alters Insulin Signaling, Enhances Lipogenesis and ROS Production, and Induces Mitochrondrial Dysfunction", *Diabetes*, vol. 60, pp. 258-268 (2011).
Costa et al. "Antioxidant Activity and Inhibition of Human Neutrophil Oxidative Burst Mediated by Arylopropionic Acid Non-steroidal Anti-inflammatory Drugs," *Biol. Pharm. Bull* 29(8), pp. 1659-1670 (2006).

* cited by examiner

*Primary Examiner* — Dennis Heyer
(74) *Attorney, Agent, or Firm* — Leydig, Voit & Mayer, Ltd.

(57) ABSTRACT

A method of increasing PGC-1α expression in a mammalian cell, the method comprising administering an effective amount of indoprofen, a pharmaceutically acceptable salt thereof, or a solvate thereof to the cell.

11 Claims, 11 Drawing Sheets

(A)

(B)

(A)       Control          Indoprofen (B)        Qua  GAS  TA  EDL  Sol

Control

Indoprofen
(3mg/Kg)

(C)               Heart
           Control   Indoprofen (A)

(B)

COMPOSITION INCLUDING INDOPROFEN AND USE THEREOF

CROSS-REFERENCE TO RELATED APPLICATION

This application claims the benefit of Korean Patent Application No. 10-2015-0138617, filed on Oct. 1, 2015, in the Korean Intellectual Property Office, the entire disclosure of which is hereby incorporated by reference.

BACKGROUND

1. Field

The present disclosure relates to a composition including indoprofen and use thereof and use to increase PGC-1α expression.

2. Description of the Related Art

Peroxisome proliferator-activated receptor gamma coactivator-1 alpha (PGC-1α) is a transcriptional activator that binds to PPAR-gamma and many different nuclear receptors involved in the expression of several genes. PGC-1α expression is increased in muscle cells in response to exercise in order to promote mitochondrial biogenesis and angiogenesis in muscles and to increase the proportion of oxidative muscle fibers in skeletal muscles.

The importance of PGC-1α expression and oxidative muscle fiber has been revealed in many studies. Reduced PGC-1α expression is observed in the muscles of obese or aging individuals. In PGC-1α-deficient mice, the reduction in oxidative muscle fiber and mitochondrial function is known to cause metabolic diseases associated with obesity as well as a decrease in the capacity of muscle.

Therefore, there is a need to develop compositions and methods to increase PGC-1α expression. This invention provides such compositions and methods.

SUMMARY

An aspect provides a composition for increasing PGC-1α expression in a mammalian cell, the composition including indoprofen, a pharmaceutically acceptable salt thereof, or a solvate thereof as an active ingredient.

Another aspect provides a composition for converting muscle type II into muscle type I or increasing muscle type I, or strengthening muscles or increasing the exercise performance in a subject, the composition including indoprofen, a pharmaceutically acceptable salt thereof, or a solvate thereof as an active ingredient.

Still another aspect provides a method of increasing PGC-1α expression in a mammalian cell, the method including administering an effective amount of indoprofen, a pharmaceutically acceptable salt thereof, or a solvate thereof to a mammalian cell or subject comprising the mammalian cell.

Still another aspect provides a method of converting muscle type II into muscle type I, increasing muscle type I, strengthening muscles, or increasing the exercise performance in a subject, the method including administering an effective amount of indoprofen, a pharmaceutically acceptable salt thereof, or a solvate thereof to the subject.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
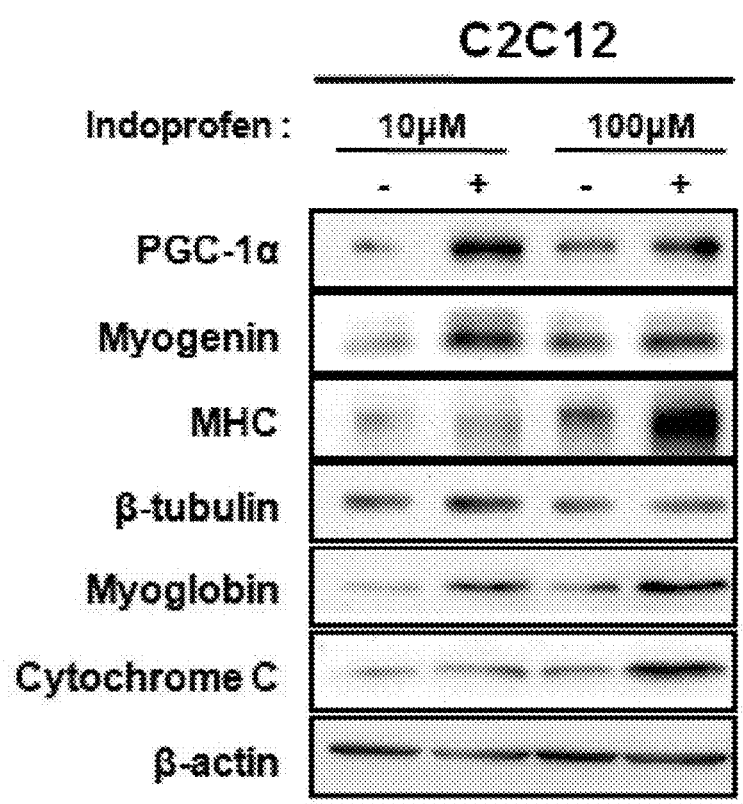
FIG. 1 shows expression changes of PGC-1α, muscle differentiation markers, myogenin and myosin heavy chain (MHC), myoglobin, and a mitochondrial protein, cytochrome C in myoblasts according to indoprofen concentration.

One aspect of the invention provides a composition for increasing PGC-1α expression in a mammalian cell, the composition including indoprofen, a pharmaceutically acceptable salt thereof, or a solvate thereof as an active ingredient.

Another aspect provides a composition for converting muscle type II into muscle type I, increasing muscle type I, strengthening muscles, or increasing the exercise performance in a subject, the composition including indoprofen, a pharmaceutically acceptable salt thereof, or a solvate thereof as an active ingredient.

Indoprofen is a monocarboxylic acid which is a propionic acid having a 4-(1-oxo-1,3-dihydroisoindol-2-yl)phenyl group, and its IUPAC name is 2-[4-(1-oxo-1,3-dihydro-2H-isoindol-2-yl)phenyl]propionic acid. Indoprofen may have a structure of the following Formula I.

[Formula I]

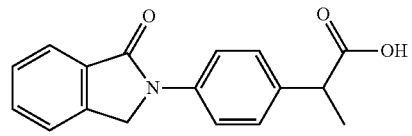

The indoprofen may be purchased from a commercially available source or directly synthesized. The term "pharmaceutically acceptable salt" may include acid addition salts, for example, salts derived from inorganic acids such as hydrochloric acid, bromic acid, sulfuric acid, sulfamic acid, phosphoric acid, or nitric acid, and salts derived from organic salts such as acetic acid, propionic acid, succinic acid, glycolic acid, stearic acid, citric acid, maleic acid, malonic acid, methanesulfonic acid, tartaric acid, malic acid, phenyl acetic acid, glutamic acid, benzoic acid, salicylic acid, 2-acetoxybenzoic acid, fumaric acid, toluene sulfonic acid, oxalic acid, or trifluoroacetic acid, which are generally used in a pharmaceutical field. Further, the salt may include general metal salts, for example, salts derived from metals such as lithium, sodium, potassium, magnesium, or calcium. The acid addition salt or the metal salt may be prepared by a common method.

The term "solvate" refers to a complex or an aggregate formed by one or more solute molecules, indoprofen, or pharmaceutically acceptable salts thereof and one or more solvent molecules. The solvate may be a complex or an aggregate formed with, for example, water, methanol, ethanol, isopropanol, or acetic acid.

The indoprofen may also exist in the form of a stereoisomer thereof. The stereoisomer may include all stereoisomers such as enantiomers and diastereomers. The indoprofen may be a stereoisomerically pure form or a mixture of one or more stereoisomers, for example, a racemic mixture. Separation of a particular stereoisomer may be performed by one of the general methods known in the art.

The composition may include indoprofen, a pharmaceutically acceptable salt thereof, or a solvate thereof in "an effective amount". In the composition, the "effective amount" may be an amount sufficient to increase PGC-1α expression in a cell. The effective amount may be also an amount sufficient to convert muscle type II into muscle type I or to increase muscle type I. The effective amount may be also an amount sufficient to strengthen muscles or to increase the exercise performance in a mammal. The effective amount may be also an amount sufficient to treat or prevent sarcopenia, muscular atrophy, obesity or diabetes.

The term "treatment" means an amount sufficient to exhibit a therapeutic effect when administered to a subject in need of treatment. The term "treatment" means treatment of a disease or a medical symptom of a subject, for example, a mammal including a human, and it includes: (a) prevention of occurrence of a disease or a medical symptom, that is, prophylactic treatment of a patient; (b) alleviation of a disease or a medical symptom, that is, removal or recovery of the disease or medical symptom in a patient; (c) inhibition of a disease or a medical symptom, that is, delay or halt of progression of a disease or a medical symptom of a subject; or (d) relief of a disease or a medical symptom of a subject.

The term "prevent" means prevention of occurrence of a disease or a medical symptom by prophylactic treatment of a patient. Subjects in need of prophylactic treatment can be readily identified by a person of ordinary skill in the art. For example, subjects put on long term bed rest or subjects with diabetes would be candidates for prophylactic treatment.

The "effective amount" may be properly selected by those skilled in the art. By way of non-limiting examples, "effective amount" may be about 0.01 mg to about 10,000 mg, about 0.1 mg to about 1000 mg, about 1 mg to about 100 mg, about 0.01 mg to about 1000 mg, about 0.01 mg to about 100 mg, about 0.01 mg to about 10 mg, or about 0.01 mg to about 1 mg per composition.

The composition may be a pharmaceutical composition or a food composition.

If the composition is a pharmaceutical composition, the composition may further include a pharmaceutically acceptable diluent or carrier. The carrier may be an excipient, a disintegrating agent, a binder, a lubricant, or a combination thereof. The composition may have a formulation for oral or parenteral administration. The formulation for oral administration may be a granule, powder, a liquid, a tablet, a capsule, a dry syrup, or a combination thereof. The formulation for parenteral administration may be an injectable formulation or a formulation for external use on the skin. The formulation for skin external use may be a cream, a gel, an ointment, a skin emulsifier, a skin suspension, a transdermal patch, a drug-containing bandage, a lotion, or a combination thereof.

If the composition is a food composition, the composition may include one or more additives. The additive may include a concentrated fruit juice or powder fruit juice; water-soluble or fat-soluble vitamins; a flavoring agent; amino acids, nucleic acids or salts thereof; plant fibers; or minerals. The compositions may be formulated in a variety of forms such as powder, a granule, a tablet, a capsule, a drink, etc.

In the above aspects, the composition may be used to treat a "muscle wasting disease". The term "muscle wasting disease" means a disease or a condition accompanied by a gradual decrease in muscle mass. The muscle may be skeletal muscle. The muscle wasting disease may be sarcopenia or muscular atrophy. Sarcopenia is the degenerative loss of skeletal muscle mass, quality, and/or strength associated with aging. The degenerative loss of skeletal muscle mass may be, for example, 0.5-1% loss of skeletal muscle mass per year after the age of 50. The muscular atrophy is caused by progressive degeneration of skeletal muscle fibers.

The muscle wasting disease may be caused by various factors. The muscle wasting disease may be, for example, sarcopenia caused by aging, sarcopenia caused by diabetes, sarcopenia caused by obesity, muscular atrophy caused by aging, muscular atrophy caused by long-term bed rest, muscular atrophy caused by an assistive device for therapy, or muscular atrophy caused by cachexia. The composition may be administered to a subject having the "muscle wasting disease".

The composition may prevent muscle loss, promote muscle regeneration or differentiation, improve exercise performance, improve metabolism, or a combination thereof.

A muscle cell or muscle fiber forming a skeletal muscle may be classified into type I muscle fiber called red muscle fiber or slow-twitch muscle fiber, and type II muscle fiber called white muscle fiber or fast-twitch muscle fiber. Type I muscle fiber appears red due to the high levels of myoglobin, and includes a large number of mitochondria and oxidase to utilize aerobic metabolism. Type I muscle fiber is characterized by slow contraction and high resistance to fatigue, and used in endurance aerobic exercise. Type II muscle fiber appears white due to the low levels of myoglobin. Type II muscle fiber is characterized by fast contraction, and is efficient for short bursts of speed and strength, but has low resistance to fatigue. The composition converts type II into type I among muscle fibers constituting skeletal muscles or promotes the conversion, or increases the amount of type I muscle fiber.

The improvement of metabolism may include an increase in energy expenditure, an increase in glucose tolerance, and/or a decrease in body fat content.

Still another aspect provides a method of increasing PGC-1α expression in a mammalian cell, the method including administering an effective amount of indoprofen, a pharmaceutically acceptable salt thereof, or a solvate to the cell. The effective amount is sufficient to increase PGC-1α expression in a mammalian cell. The cell may be a muscle cell. The muscle cell may be a skeletal muscle cell. The muscle cell may be a quadriceps muscle (Quad), a gastrocnemius muscle (GAS) cell, a tibialis anterior muscle (TA) cell, an extensor digitorum longus muscle (EDL) cell, or a soleus muscle (SOL) cell. The cell may be in a subject. The administration of indoprofen, a pharmaceutically acceptable salt thereof, or a solvate to the cell may be achieved by administering the indoprofen or salt or solvate thereof to the subject.

Administration may mean administration to a subject who exhibits the low expression of PGC-1α in a cell of the subject. Further, the administration may mean administration to a subject having or afflicted by a disease caused by the low expression of PGC-1α. The low expression of PGC-1α may be an expression level of PGC-1α gene that is lower than that of a muscle cell derived from a control subject, for example, a healthy person, or an expression level of PGC-1α gene in a subject that is low compared to that of the same subject before a predetermined period, for example, before about 1 year, about 300 days, about 200 days, about 100 days, about 50 days, about 30 days, or about 10 days in the same person, or a low expression level of PGC-1α gene can be a level that is lower than a predetermined level (e.g., the level of a normal healthy person, or average level of a group of normal healthy persons). The low expression of PGC-1α may include no expression of PGC-1α gene.

The administration may result in prevention or treatment of the disease caused by the low expression of PGC-1α. The disease may be a muscle wasting disease. The disease may include sarcopenia, muscular atrophy, obesity and/or diabetes. The muscular atrophy may be non-inherited. The muscular atrophy may be caused by aging, long-term bed rest, an assistive device for therapy, and/or cachexia. The muscular atrophy may not be related to or caused by a deletion or a mutation of Survival Motor Neuron (SMN) gene. Also, the administration of indoprofen or salt or solvate thereof may prevent muscle loss, promote muscle regeneration or differentiation, improve exercise performance, improve metabolism, or a combination thereof, in the subject.

Still another aspect provides a method of converting muscle type II into muscle type I, increasing muscle type I, strengthening muscles, or increasing the exercise performance in a subject, the method including administering an effective amount of indoprofen, a pharmaceutically acceptable salt thereof, or a solvate to a subject. The effective amount may be an amount sufficient to convert muscle type II into muscle type I, to promote the conversion, or to otherwise cause an increase in muscle type I. The administration may be administration to a subject in which the amount of muscle type I is reduced compared to that of a control subject (e.g., a normal healthy person), or compared to the level of type I in the same person taken before a predetermined period, for example, before about 1 year, about 300 days, about 200 days, about 100 days, about 50 days, about 30 days, or about 10 days, or compared to a predetermined level (e.g., the level of a normal healthy person, or average level of a group of normal healthy persons). The effective amount may be an amount sufficient to strengthen muscles or to increase the exercise performance in a mammal. The strengthening muscle may be a relative high level of type I, compared to type II, a high oxidative metabolism, a high grip strength, or a combination thereof. The administration may be administration to a subject in which the muscles are weakened or the exercise performance is decreased. The weakening may be a relative low level of type I, a low oxidative metabolism, a low grip strength, or a combination thereof, compared to that of a muscle cell derived from a control subject (e.g., a healthy person), a relative low level of type I, a low oxidative metabolism, a low grip strength, or a combination thereof, compared to that measurement in the same person taken before a predetermined period, for example, before about 1 year, about 300 days, about 200 days, about 100 days, about 50 days, about 30 days, or about 10 days, or a relatively low level of type I, a low oxidative metabolism, a low grip strength, or a combination thereof, compared to a predetermined level. The subject may be a subject suffering from hypokinesia due to muscle injury.

In the above aspects, the administration may be performed by any method known in the art. The administration may be, for example, intravenous, intramuscular, oral, transdermal, mucosal, intranasal, intratracheal, or subcutaneous administration. The administration may be systemic or topical administration. The administration may be local and/or topical administration to a site in which exercise performance is reduced. The administration may be administration to muscle tissues. The administration may be administration to skeletal muscles. The subject may be a person aged 50 years or over, or a person aged 60 years or over, for example, a person aged about 50 years to about 100 years, about 60 years to about 100 years, about 70 years to about 100 years, about 80 years to about 100 years, about 90 years to about 100 years, about 60 years to about 90 years, about 60 years to about 80 years, or about 60 years to about 70 years. The muscles may be skeletal muscles. The skeletal muscles may be facial muscles, neck muscles, abdominal muscles, back muscles, pectoral muscles, upper limb muscles, or lower limb muscles. The lower limb muscles may be quadriceps muscle (Quad), gastrocnemius muscles (GAS), tibialis anterior muscles (TA), extensor digitorum longus muscles (EDL), or soleus muscles (SOL).

In the above aspects, the administration may be performed by administration in an amount of about 0.1 mg to about 1,000 mg, about 0.1 mg to about 500 mg, about 0.1 mg to about 100 mg, about 0.1 mg to about 50 mg, about 0.1 mg to about 25 mg, about 1 mg to about 1,000 mg, about 1 mg to about 500 mg, about 1 mg to about 100 mg, about 1 mg to about 50 mg, about 1 mg to about 25 mg, about 5 mg to about 1,000 mg, about 5 mg to about 500 mg, about 5 mg to about 100 mg, about 5 mg to about 50 mg, about 5 mg to about 25 mg, about 10 mg to about 1,000 mg, about 10 mg to about 500 mg, about 10 mg to about 100 mg, about 10 mg to about 50 mg, or about 10 mg to about 25 mg per kg of body weight per day.

In the above aspects, the subject may be a mammal, for example, a human, a cow, a horse, a pig, a dog, a sheep, a goat, or a cat. The subject may be a mammal excluding a human. The subject may be a subject in need of increasing red muscle fiber, slow-twitch muscle fiber, or type I muscle fiber.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in more detail with reference to Examples. However, these Examples are for illustrative purposes only, and the scope of the present invention is not intended to be limited by these Examples.

Example 1: Screening of PGC1-α Activator

1. Establishment of PGC-1α Reporter-Expressing C2C12 Myoblast

C2C12 myoblast cells were purchased from ATCC (Cat no. CRL-1722, American Type Culture Collection, USA). To screen a compound activating PGC-1α gene expression in C2C12 myoblast cells, a PGC-1α reporter-expressing C2C12 cell line (hereinafter, referred to as 'PGC-1α reporter cell line' or 'C2C12-PGC-1α cell line) was established. A vector expressing luciferase and dscGFP (destabilized Green Fluorescent Protein) under a human PGC-1α promoter having a length of 1 kb was prepared, and this vector was inserted into lentivirus to transfect C2C12 cells. To select a cell line that genetically stably expressed the vector, fluorescence emitted from green fluorescent protein (GFP) included in the vector was monitored. 5 µg/ml of puromycin, a selection marker for the vector, was added to a cell culture medium, and a cell line expressing PGC-1α reporter was selected. Luciferase expression level in the PGC-1α reporter cell line depends on a stimulation applied to the PGC-1α promoter. That is, if a compound is a PGC-1α expression inducer, it stimulates the PGC-1α promoter to increase the luciferase expression, and if a compound is a PGC-1α expression inhibitor, the luciferase expression is decreased. The expression level is measured by luminescence after addition of a luciferase substrate, thereby determining activation or inhibition of PGC-1α transcription by the compound.

2. Screening of Compound Using PGC-1α Reporter Cell Line

The C2C12-PGC-1α reporter cell line prepared in Section 1 was used to screen a PGC-1α expression regulator from 2320 compounds provided by Korea Chemical Bank. In detail, C2C12-PGC-1α reporter cells were cultured in each well of 96-well plate containing Dulbecco's modified Eagle's medium (DMEM, Gibco) supplemented with 10% fetal bovine serum (FBS) in a 5% $CO_2$ incubator until they reach 70% confluence by changing the medium every 2 days. Thereafter, 2320 compounds are dissolved in DMSO at a final concentration of 10 µM, and then added to each well. 48 hours later, luminescence by luciferase was measured. In detail, cells were lysed in 10 µl of a passive lysis buffer (50 mM Tris-HCl, 7.5 mM $MgCl_2$, 750 mM NaCl, 5 mM EGTA, 1% Triton-x 100, 1 mM $Na_3VO_4$, 10 mM NaF, 0.1 mM phenylmethanesulfonylfluoride (PMSF), protease inhibitor (PI)) as a cell lysis buffer, and 50 µl of a luciferase substrate, luciferin was added thereto to allow enzymatic reaction. Then, luminescence is measured. The measured values were normalized to each well and plate, and a value measured in a well treated with a solvent of the compound, DMSO, is used as a control group to express the value as a relative ratio. The PGC-1α promoter activity of 2320 compounds was measured, and as a result, 8 compounds ranked in the top 1.5%, which show promoter activity twice or higher than that of a control group DMSO, were selected. Among the 8 compounds, indoprofen greatly increased the PGC-1α promoter activity and has been shown to be safe. Therefore, indoprofen was selected as the candidate material. A lethal dose (LD)-50 of indoprofen for 50% mouse mortality is 700 mg per mouse body weight (kg). For reference, ID50 of aspirin is 250 mg/kg.

Example 2: Effect of Indoprofen on Myoblast

1. Analysis of PGC-1α, Differentiation Marker, and Mitochondrial Protein Expressions in Indoprofen-Treated Myoblasts The effect of indoprofen on the differentiation of C2C12 myoblasts into muscle cells was analyzed. Dulbecco's Modified Eagle Medium (DMEM) supplemented with 15% fetal bovine serum was used as a growth medium for the culture of C2C12 myoblasts, and DMEM supplemented with 2% horse serum was used as a differentiation medium for differentiation into muscle cells. To induce differentiation of C2C12 myoblasts into muscle cells, 10 µM or 100 µM indoprofen dissolved in DMSO was added to the experimental groups, and DMSO alone was added to the control group. The cells were cultured for 48 hours to induce differentiation, and then a RIPA buffer (50 mM Tris-HCl, pH 7.5, 150 mM NaCl, 1% Triton X100, 0.1% SDS, 2 mM EDTA, 0.5% sodium deoxycholate, Proteinase Inhibitor) was added to the harvested cells to allow lysis for 30 minutes, followed by centrifugation at 13,000 rpm for 30 minutes. The amount of protein in the cell lysis sample was quantified and an equal amount of protein was subjected to 7% or 15% SDS-PAGE. The protein was transferred onto a PVDF membrane, and then incubated in a blocking buffer containing 5% skim milk for 1 hour. Primary antibodies specific to individual proteins, diluted in 5% BSA, are reacted with the membrane at 4° C. for 12 hours, and then the membrane was washed with a wash buffer for 5 minutes three times. Secondary antibodies were diluted with the blocking buffer and allowed to react with the membrane at room temperature for 1 hour. Thereafter, the membrane was washed with the wash buffer for 5 minutes three times, and then exposed to X-ray film using an ECL reagent (Roche) to confirm protein expression levels.

FIG. 1 shows expression changes of PGC-1α, muscle differentiation markers, myogenin and myosin heavy chain (MHC), myoglobin, and a mitochondrial protein, cytochrome C in myoblasts according to indoprofen concentration. Myoglobin is a protein present in the heart and skeletal muscle and plays a role in the transportation of blood oxygen to muscle tissue. As shown in FIG. 1, expression of PGC-1α, muscle differentiation markers, myogenin and MHC, myoglobin, and a mitochondrial protein, cytochrome C are greatly increased in myoblasts cultured in the presence of 10 µM or 100 µM indoprofen, compared to a control group. Indoprofen shows optimal activity at 100 µM.

The result of FIG. 1 indicates that indoprofen acts as a PGC-1α inducer in muscle cells and promotes differentiation of myoblast into muscle, and also indicates that indoprofen converts muscles into oxidative muscles and promotes mitochondrial metabolism.

2. Differentiation of Indoprofen-Treated Myoblast

C2C12 myoblasts were treated with 10 µM or 100 µM indoprofen and allowed to differentiate for 3 days. A control group was treated with DMSO alone. Fluorescence staining of C2C12 myotubes was performed using MHC antibody. The number of nuclei within one myotube was counted by DAPI staining. C2C12 cells were differentiated in DMED supplemented with 2% horse serum for 72 hours. The cells were washed with 1×PBS, and then fixed in 4% paraformaldehyde at room temperature for 15 minutes, followed by washing with 1×PBS three times. The cells were reacted with a permeabilizing buffer supplemented with 0.2% Triton-X for 10 minutes, and then washed with 1×PBS three times, followed by blocking using 5% fetal bovine serum at room temperature for 1 hour. A primary antibody, anti-MHC, was diluted with 5% goat serum at a ratio of 1:500 and allowed to react at 4° C. for 12 hours, followed by washing with 1×PBS three times. A secondary antibody, anti-mouse IgG-HRP 594 (Invitrogen) was diluted with 5% goat serum at a ratio of 1:500 and allowed to react at 4° C. for 1 hour, followed by washing with 1×PBS three times. DAPI is diluted with 1×PBS at a ratio of 1:10000 and allowed to react for 1 minute, followed by washing with 1×PBS and fluorescence microscopy.

Figure 2:
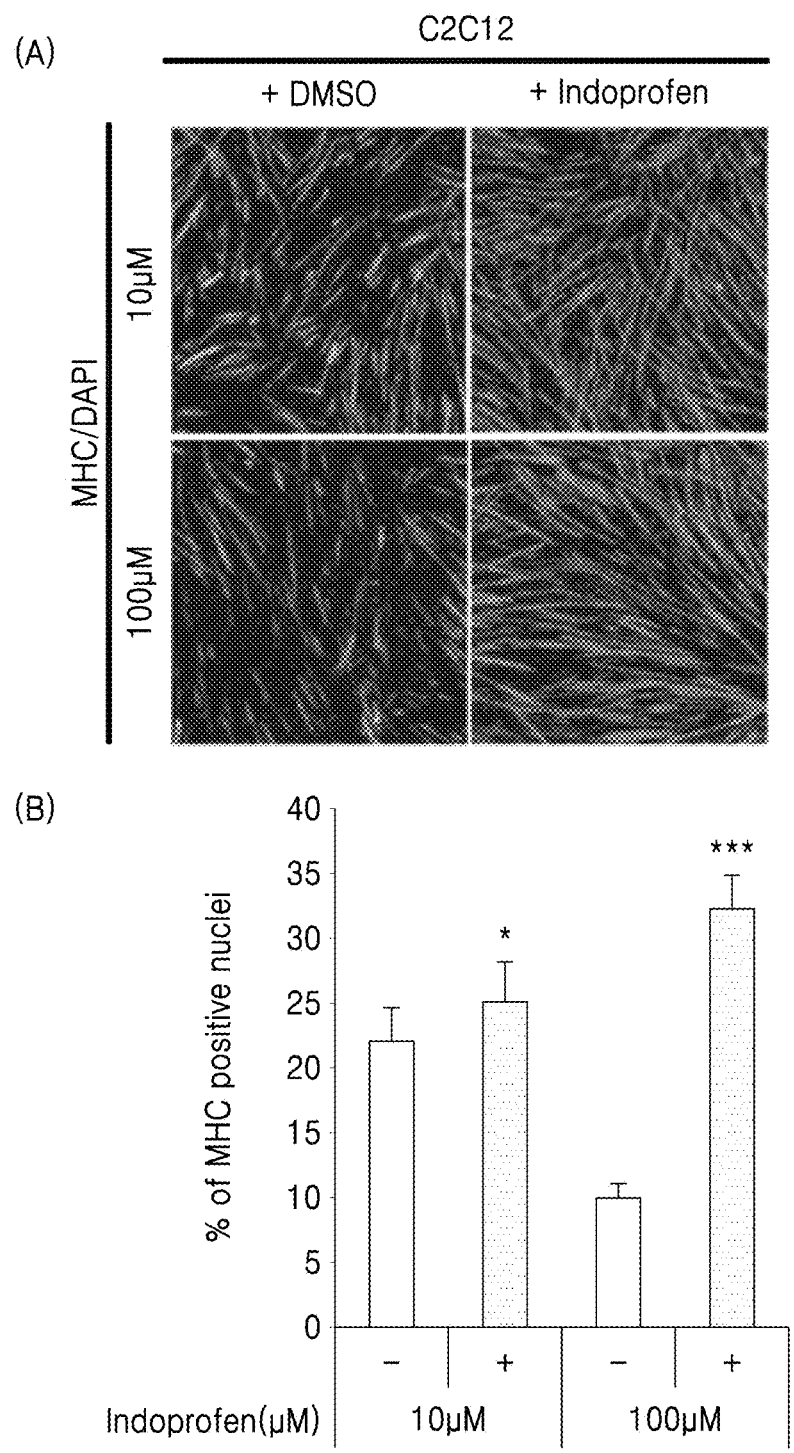
FIG. 2 shows differentiation of indoprofen-treated myoblasts, wherein panel (A) shows the result of fluorescence staining of C2C12 myotube using MHC antibody, and panel (B) shows the percentage of nuclei labeled with MHC antibody.

FIG. 2 shows differentiation of indoprofen-treated myoblasts. (A) represents the result of fluorescence staining of C2C12 myotube using MHC antibody. (B) represents a percentage of the nuclei labeled with MHC antibody. As shown in FIG. 2, when myoblasts are treated with 10 μM or 100 μM indoprofen, a percentage of the nuclei labeled with MHC antibody is significantly increased, compared to a control group, and myotube formation and fusion of myoblasts are increased, indicating that indoprofen promotes myoblast differentiation.

Example 3: Effect of Indoprofen on Animal Muscle

1. Analysis of PGC-1α Expression in Indoprofen-Treated Mouse 10 week-old C57BL/6 female mice were bred at a temperature of 22±2° C., humidity of 55±5%, and a light-dark cycle of 12:12 hours. Mice were orally administered 1.5 mg/kg of indoprofen in 100 μl of PBS twice a day. A control group was orally administered with 100 μl of PBS twice a day. The mice were allowed free access to drinking water. Skeletal muscles were separated from the mice fed with indoprofen for 2 weeks, and subjected to immunoblot analysis.

Figure 3A:
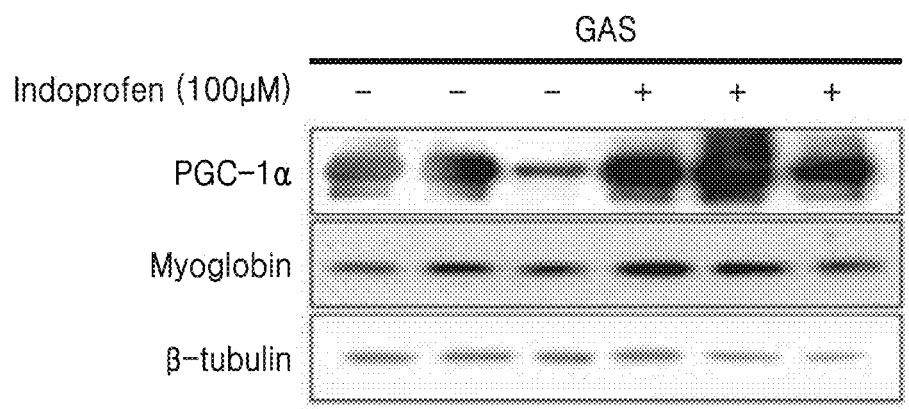
FIG. 3A shows immunoblotting of tibialis anterior muscles of mice administered with indoprofen, and quantification results thereof, wherein panel (A) shows an image of a membrane obtained by Western blotting, and panel (B) shows relative protein expression obtained by quantifying the PGC-1α band and the myoglobin band in the Western blotting image of panel (A) and comparing them to the value of a non-indoprofen treated mouse.
Figure 3A:
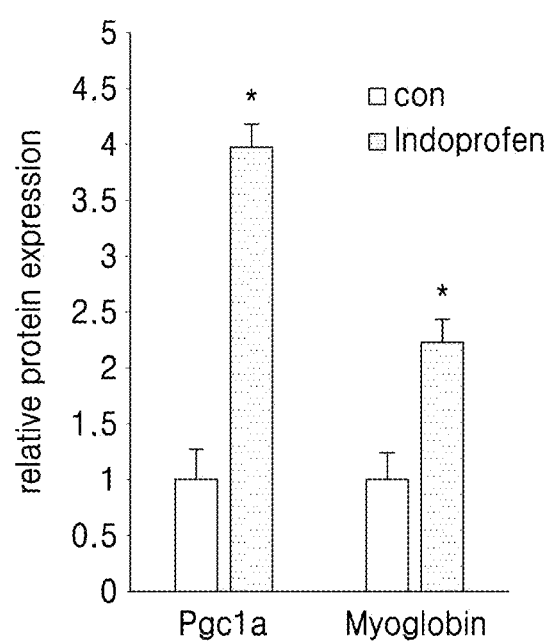

FIG. 3A shows immunoblotting of tibialis anterior muscles of mice administered with indoprofen, and quantification results thereof. *Standard error of measurement indicates P<0.05. In FIG. 3A, (A) shows an image of a membrane obtained by Western blotting, (B) shows a relative protein expression obtained by quantifying a PGC-1α band and a myoglobin band in the Western blotting image of (A) and comparing them to the value of a non-indoprofen treated mouse. As shown in FIG. 3A, expression of PGC-1α and a mitochondrial protein, myoglobin are increased, compared to the control group, indicating that increased expression of PGC-1α by administration of indoprofen increases expression of myoglobin in skeletal muscles.

2. Observation of Muscle Change in Indoprofen-Treated Mouse

To evaluate functional consequence of PGC-1α increased by indoprofen treatment of skeletal muscle, lower limb muscles and organs of mice fed with indoprofen for 2 weeks were separated and analyzed.

Figure 3B:
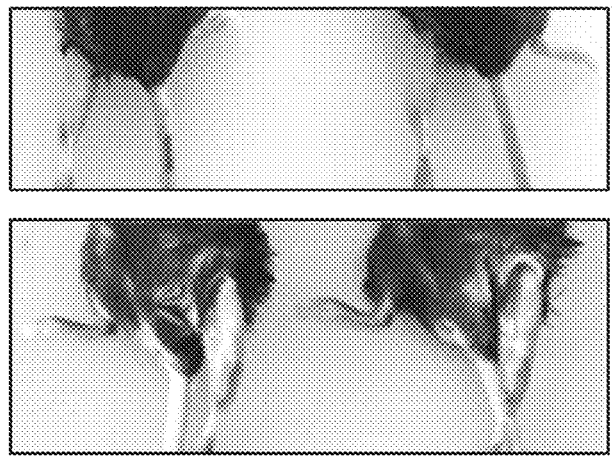
FIG. 3B shows results of observing lower limb muscles of mice administered with indoprofen, wherein panel (A) is an image showing lower limb muscles of a control group and an experimental mouse, panel (B) shows 5 different muscles separated from mice, and panel (C) indicates no change in the heart size by indoprofen treatment.
Figure 3B:
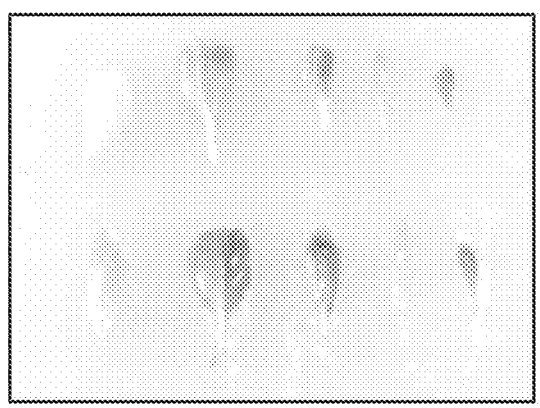
Figure 3B:

FIG. 3B shows results of observing lower limb muscles of mice administered with indoprofen. In FIG. 3B, (A) is an image showing lower limb muscles of a control group and an experimental mouse, (B) shows 5 different muscles separated from mice, that is, Quad, GAS, TA, EDL, and Sol. Herein, Quad indicates quadriceps muscle, GAS indicates gastrocnemius muscle, TA indicates tibialis anterior muscle, EDL indicates extensor digitorum longus muscle, and SOL indicates soleus muscle. (C) indicates no change in the heart size by indoprofen treatment.

Quadriceps muscle and gastrocnemius muscle exist as a white muscle because glycolytic muscle fibers are mainly distributed therein. As shown in FIG. 3B, quadriceps muscle and gastrocnemius muscle are converted to red muscles having a high percentage of oxidative muscle fibers having a relatively large number of mitochondria in the indoprofen-treated mouse, compared to the control group, indicating that increased expression of PGC-1α by indoprofen treatment increases oxidative muscle fibers, leading to conversion of white muscles to red muscles.

3. Observation of Muscle Fiber in Indoprofen-Treated Mouse

To examine distribution of 2a type muscle fiber and 2b type muscle fiber, extensor digitorum longus muscles of mice administered with indoprofen for 2 weeks were subjected to immunohistochemistry. 2a type muscle fiber is an oxidative muscle fiber type, and there are two types: aerobic, that is, oxygen-dependent energy source and anaerobic, that is, oxygen-independent energy source. 2b type muscle fiber is a glycolytic muscle fiber type, and includes only anaerobic energy source.

Frozen sections stored in a deep freezer of −80° C. were washed with 1×PBS twice, and fixed with 4% paraformaldehyde at room temperature for 15 minutes, and then washed with 1×PBS twice. The tissue and a permeabilization buffer (0.2% Triton-X/PBS) were reacted at room temperature for 30 minutes, and washed with 1×PBS twice. The tissue and Proteinase K were reacted at 37° C. for 10 minutes for antigen retrieval, and washed with 1×PBS twice, and blocked in a blocking buffer (0.1% gelatin, 5% goat serum, 0.5% BSA, and 0.1% Triton-X) for 1 hr. As a primary antibody, a rabbit antibody specifically binding to MHC2a or MHC2b was diluted with the blocking buffer at a ratio of 1:500 and reacted at 4° C. for 12 hrs, followed by washing with 1×PBS twice. A secondary antibody, anti-rabbit antibody was reacted, followed by washing 1×PBS twice. After sealing, a fluorescence microscope (Nikon, body: Ti-u, camera: DS-RI1, program: NIS-elements BR 3.1) was used for analysis.

Figure 3C:
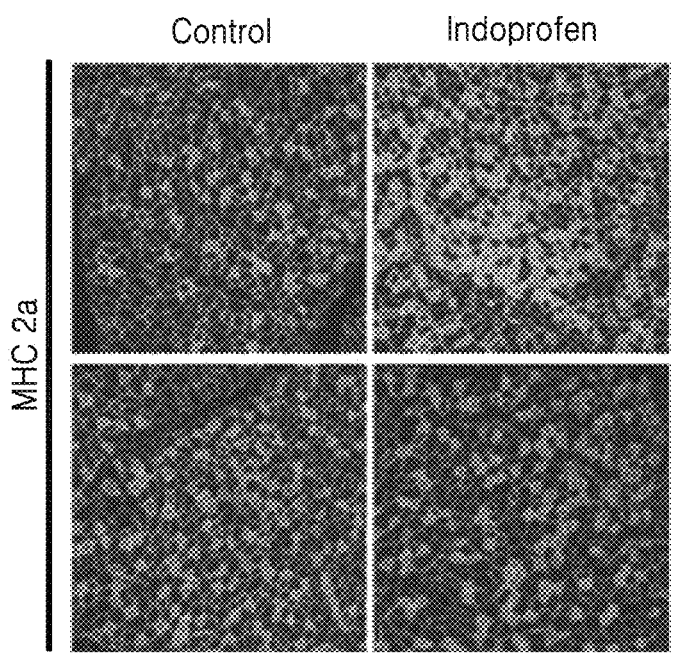
FIGS. 3C and 3D show changes in the muscle fiber type in the extensor digitorum longus muscles of mice administered with indoprofen.
Figure 3C:
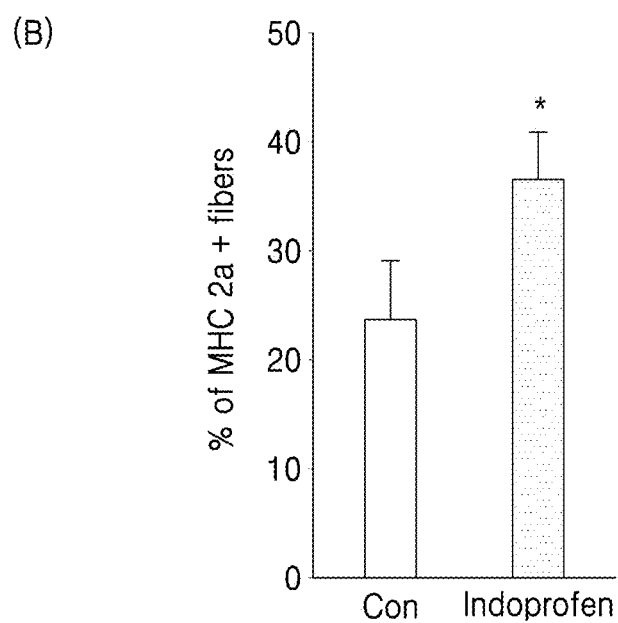
Figure 3D:
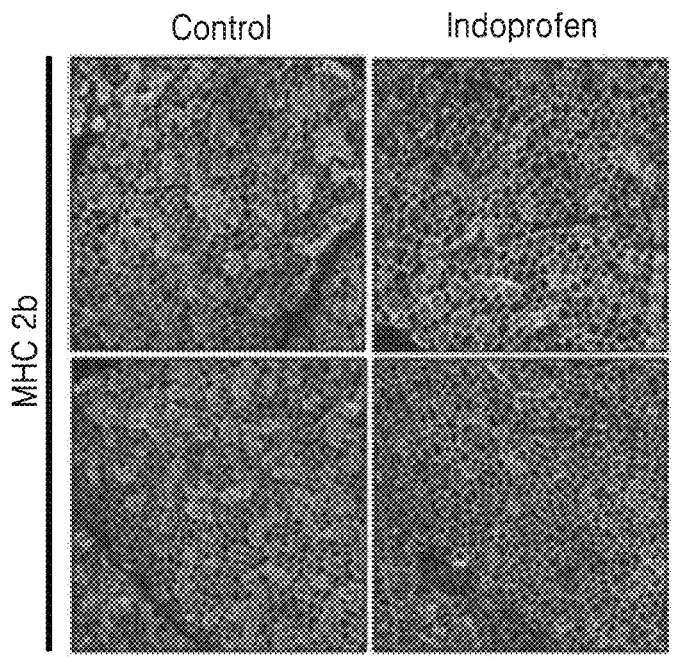
Figure 3D:
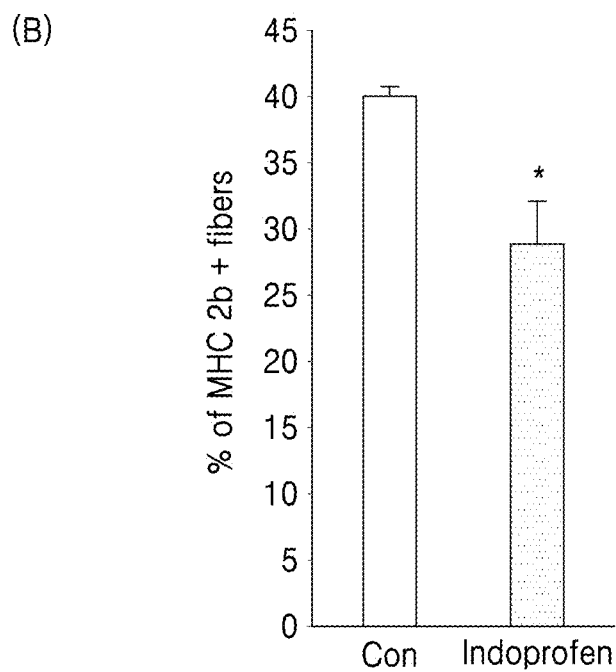

FIGS. 3C and 3D show changes of the muscle fiber type in the extensor digitorum longus muscles of indoprofen-treated mouse. FIG. 3C shows results of performing immunohistochemistry of the frozen sections of extensor digitorum longus muscles using rabbit anti-Myh2a antibody, and FIG. 3D shows results of performing immunohistochemistry of the frozen sections of extensor digitorum longus muscles using rabbit anti-Myh2b antibody. In (A) of FIGS. 3C and 3D, the green color represents muscle fibers stained with anti-Myh2a and anti-Myh2b antibody, respectively. The number of muscle fibers stained with green is counted and given in a graph of (B) of FIGS. 3C and 3D. As shown in the graph, the number of oxidative 2a type muscle fiber is increased in the extensor digitorum longus muscle of mouse orally administered with indoprofen, compared to those of the muscle of a non-indoprofen treated control mouse. In contrast, the number of glycolytic 2b type muscle fiber is decreased, indicating that indoprofen treatment increases oxidative muscle fibers having high mitochondrial activity and decreases glycolytic muscle fibers.

4. Analysis of Mitochondrial Enzyme Activity in Indoprofen-Administered Mouse

Staining of succinic dehydrogenase (SDH) and NADPH in the extensor digitorum longus muscle of a mouse administered with indoprofen for 2 weeks was performed. This staining method is a method of analyzing mitochondrial activity by measuring activities of SDH and NADPH which are enzymes involved in the electron transport chain of mitochondria. Staining degree of SDH and NADPH represents a content of oxidative muscle fiber.

Immediately after separation, extensor digitorum longus muscles were fixed in OCT compound and frozen using liquid nitrogen, and then sectioned to a thickness of 7 μm with a cryo-cut freezing microtome. After SDH staining, the frozen tissue sections were reacted in 0.2 M phosphate buffer (pH 7.4) containing SDH at 37° C. for 10 minutes, washed with distilled water, and then sealed, followed by observation. For NADPH staining, the frozen tissue sections were reacted in 3.5 mM phosphate buffer (pH 7.4) containing 0.9 mM NADH, and 1.5 mM nitro blue tetrazolium at 37° C. for 30 minutes, washed with distilled water, and then sealed, followed by observation.

Figure 3E:
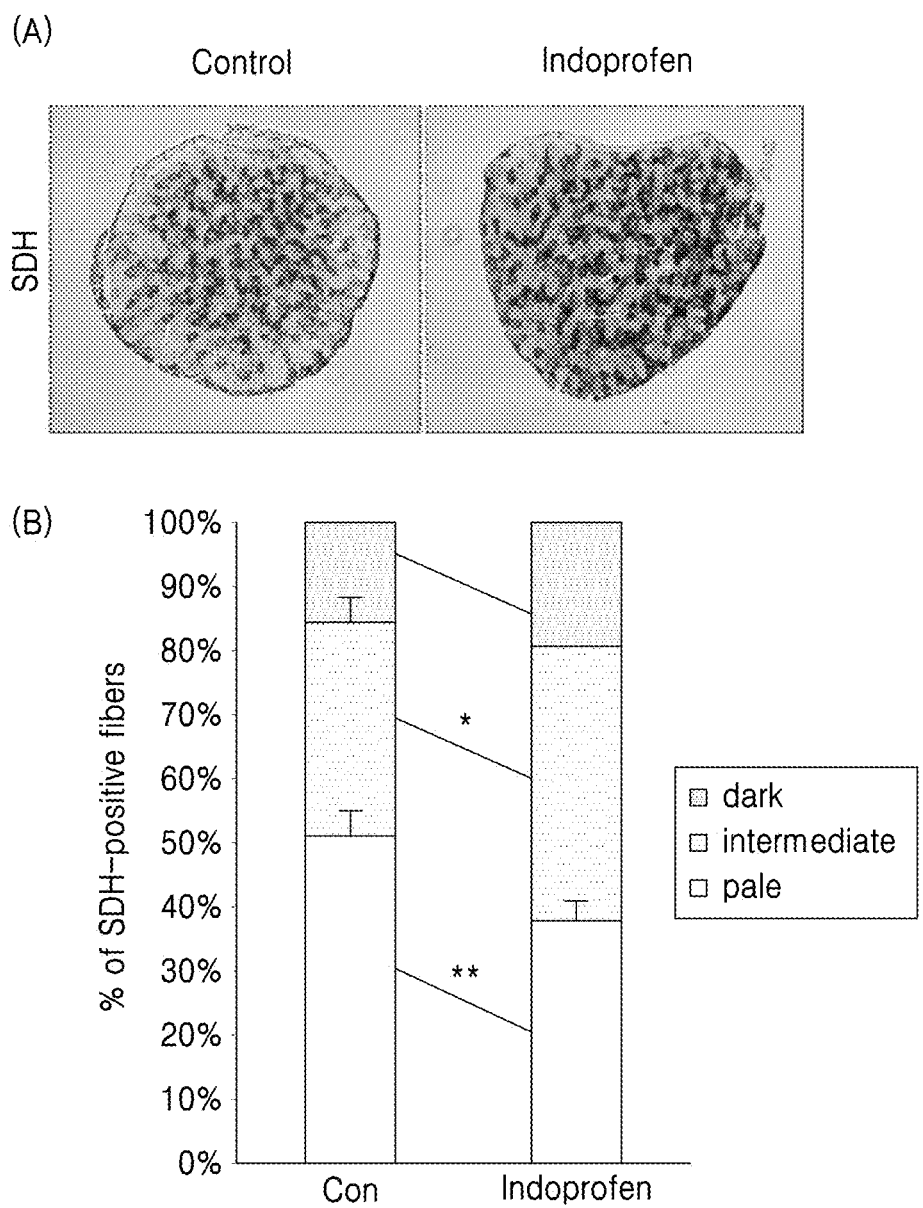
FIGS. 3E and 3F show activity changes of mitochondrial enzymes, SDH and NADPH in the extensor digitorum longus muscles of mice administered with indoprofen.
Figure 3F:
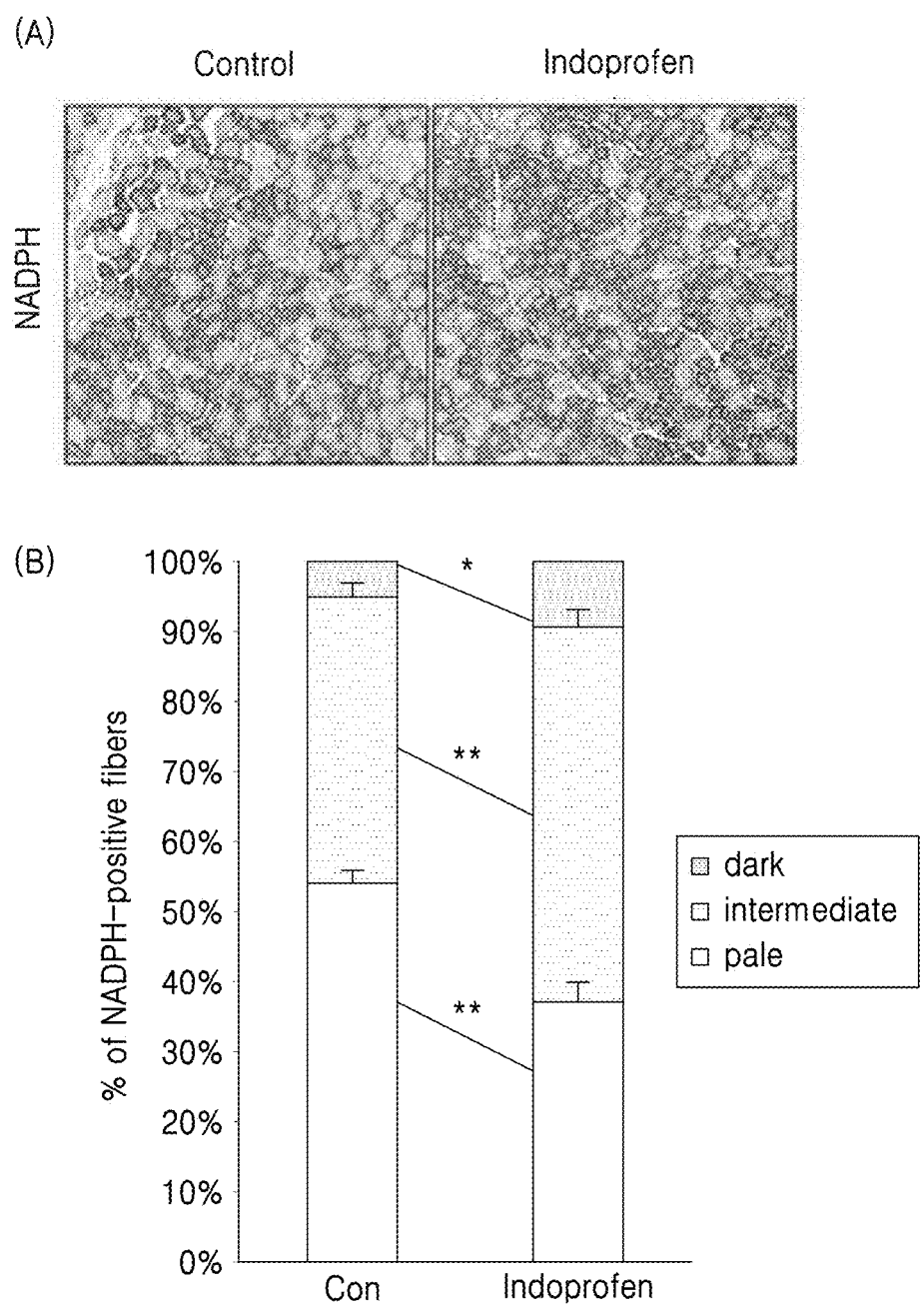

FIGS. 3E and 3F show changes in activity of mitochondrial enzymes, SDH and NADPH in the extensor digitorum longus muscle of indoprofen-administered mouse. In FIG. 3E, (A) is an image showing result of staining SDH in the frozen tissue sections, and (B) shows a percentage of stained areas of (A), which are classified into three intensities of dark, intermediate, and pale. In FIG. 3F, (A) is an image showing result of staining NADPH, and (B) shows a percentage of stained areas, which are classified into three intensities of dark, intermediate, and pale. As shown in FIGS. 3E and 3F, a percentage of muscle fiber having an increased SDH and NADPH activities is increased in the extensor digitorum longus muscle of indoprofen-administered mouse, compared to a control group, indicating that indoprofen treatment activates mitochondrial energy metabolism in muscle fibers.

The results of Examples 2 and 3 suggest that indoprofen increases PGC-1α expression in myoblasts and skeletal muscles, leading to conversion into oxidative muscle fibers having a large number of mitochondria and active energy metabolism.

Example 4: Effects of Indoprofen on Mitochondrial Enzyme Activity and Muscle in Old Animal 1. Analysis of Mitochondrial Enzyme Activity in Indoprofen-Administered Old Mouse 25-month-old female mice (weighing 30 g) were orally administered with indoprofen mixed with corn oil as an experimental group or corn oil only as a control group for 4 weeks. A 25-month-old mouse is comparable to an about 70 to 75-old human, based on a ratio of mouse average life expectancy to human average life expectancy. Staining of SDH and NADPH in extensor digitorum longus muscles of the old mice orally administered with indoprofen for 4 weeks was performed in the same manner as in 4 of Example 3.

Figure 4A:
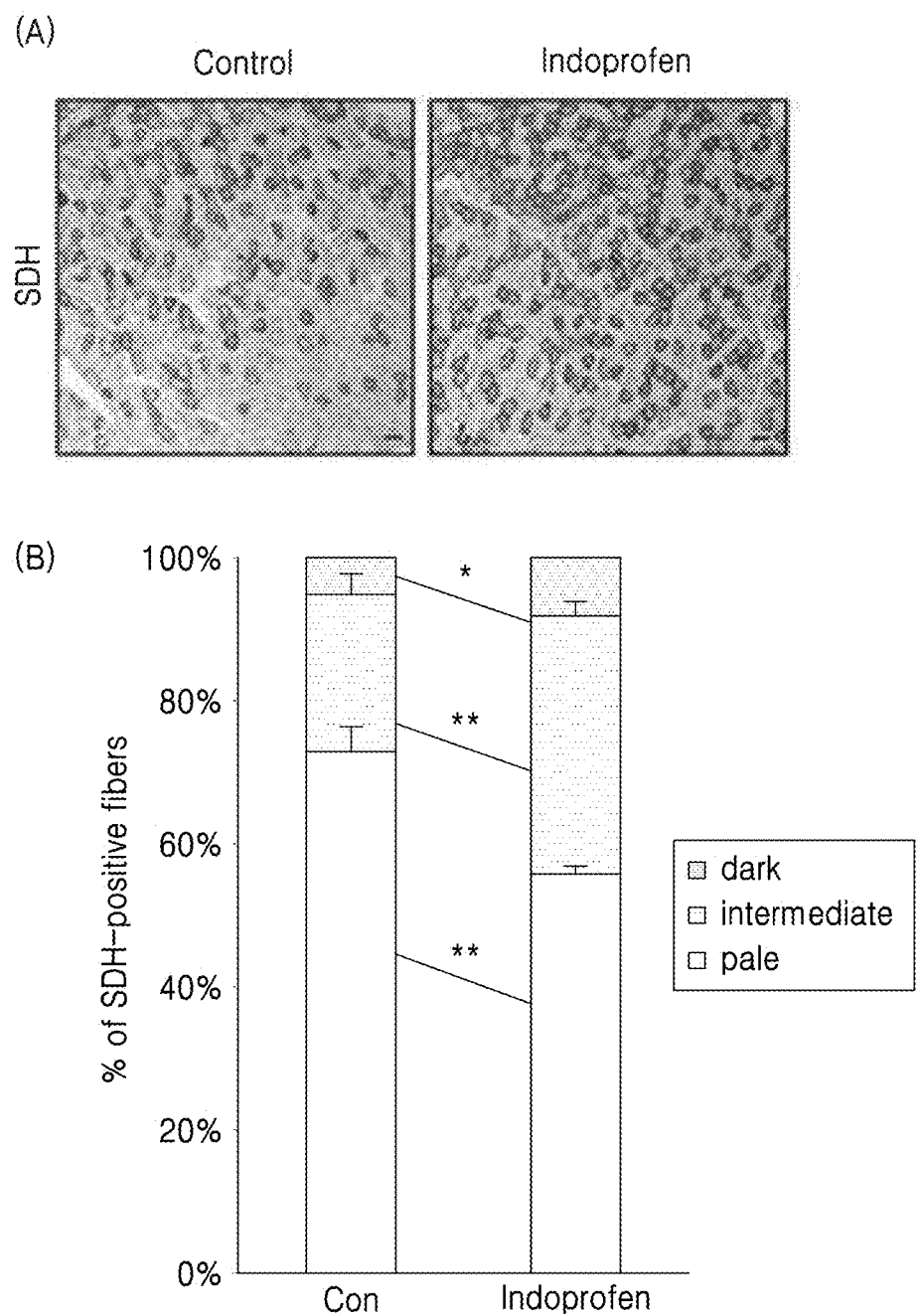
FIGS. 4A and 4B show activity changes of mitochondrial enzymes, SDH and NADPH in the extensor digitorum longus muscles of old mice administered with indoprofen.
Figure 4B:
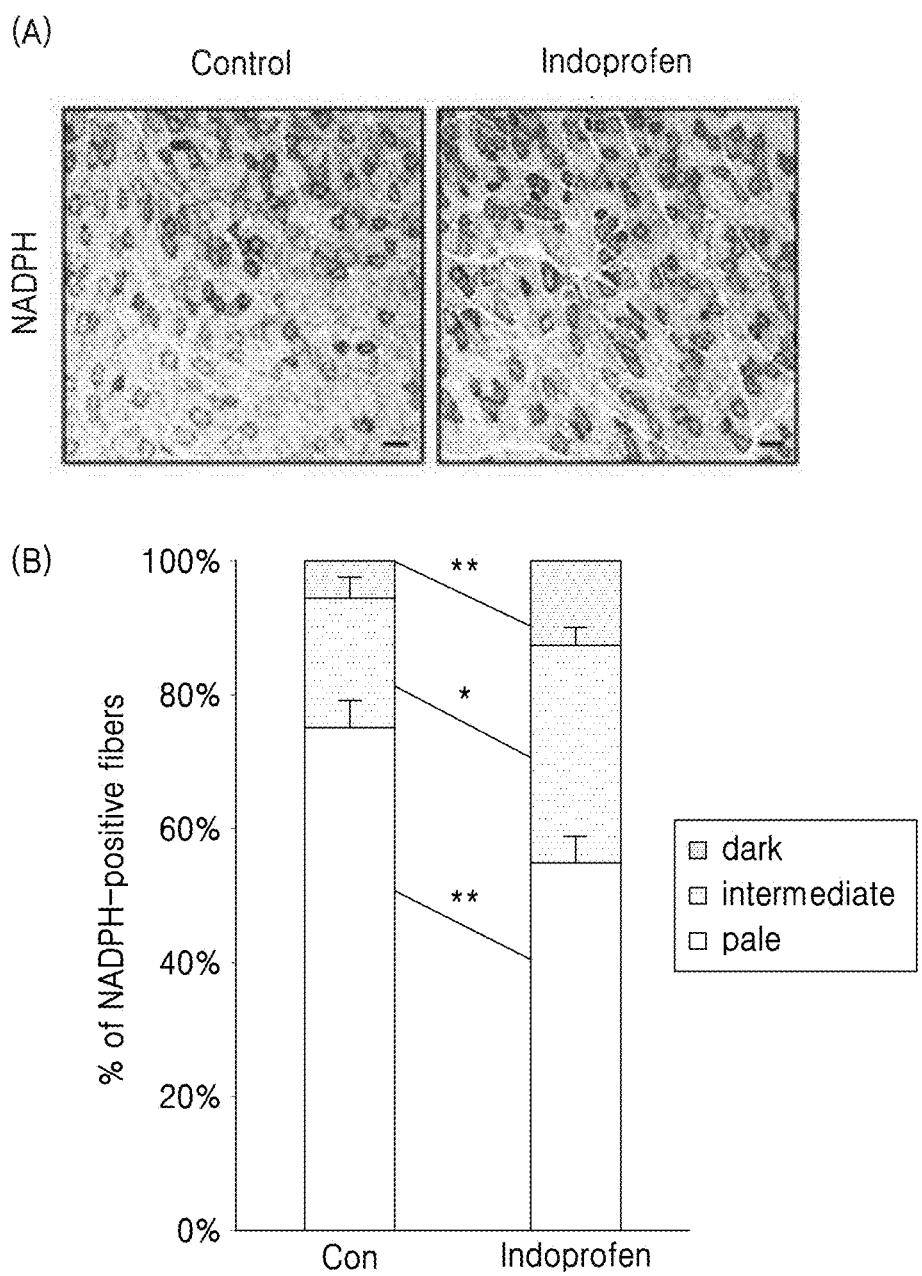

FIGS. 4A and 4B show activity changes of mitochondrial enzymes, SDH and NADPH in the extensor digitorum longus muscles of old mice administered with indoprofen. In FIG. 4A, (A) is a staining image of SDH in frozen tissue sections, and (B) shows a percentage of stained areas of (A), which are classified into three intensities of dark, intermediate, and pale. In FIG. 4B, (A) is a staining image of NADPH, and (B) shows a percentage of stained areas, which are classified into three intensities of dark, intermediate, and pale. As shown in FIGS. 4A and 4B, a percentage of muscle fiber having increased SDH and NADPH activities is increased in the extensor digitorum longus muscle of indoprofen-administered old mouse, compared to a control group, indicating that indoprofen administration also activates mitochondrial energy metabolism in muscle fibers of old animals.

2. Analysis of Changes in Muscle Weight of Indoprofen-Administered Old Mouse

To analyze changes in the muscle weight of old mouse by administration of indoprofen, lower limb muscles were separated from 25-month-old female mice (weighing 30 g) fed with indoprofen for 4 weeks.

Figure 4C:
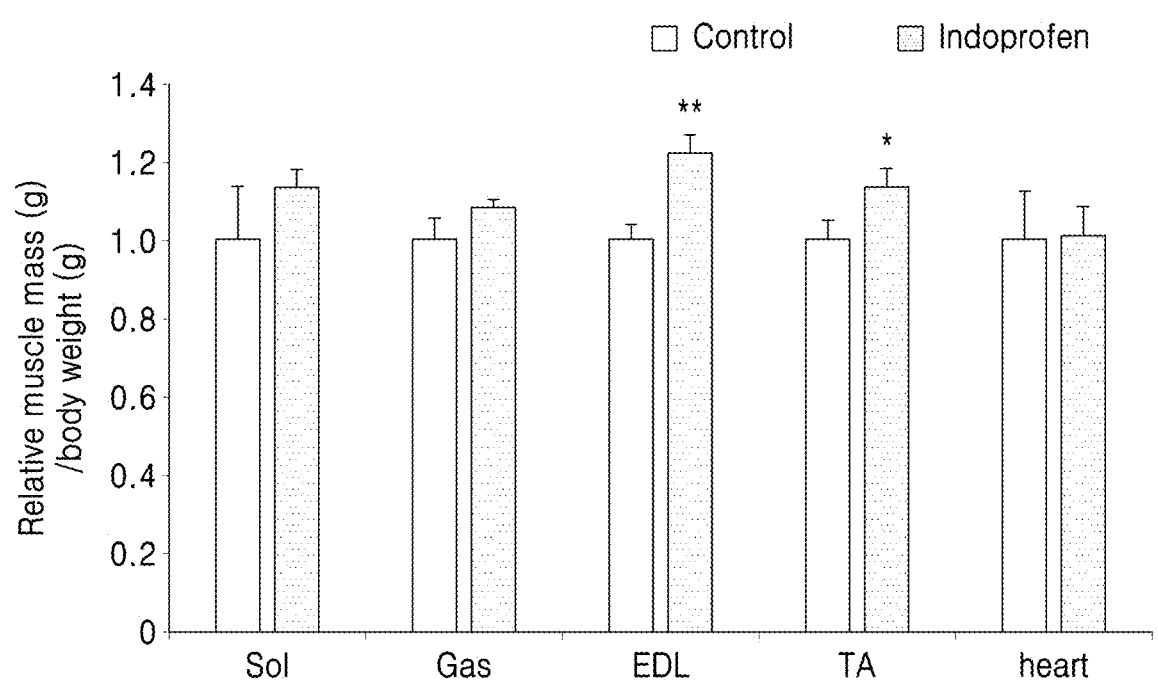
FIG. 4C shows results of weighing lower limb muscles of old mice administered with indoprofen.

FIG. 4C shows results of weighing lower limb muscles of old mice administered with indoprofen. Sol, Gas, EDL, and TA indicate soleus muscle, gastrocnemius muscle, extensor digitorum longus muscle, and tibialis anterior muscle, respectively. The result of FIG. 4C suggests that indoprofen administration increases the weight of lower limb muscle in old animals.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of increasing PGC-1α expression in a subject with low expression of PGC-1α afflicted by sarcopenia, muscular atrophy, or obesity, the method comprising administering an effective amount of indoprofen, a pharmaceutically acceptable salt thereof, or a solvate thereof to the subject.

2. The method of claim 1, wherein the administration of indoprofen, a pharmaceutically acceptable salt thereof, or a solvate thereof prevents muscle loss, promotes muscle regeneration or differentiation, improves exercise performance, improves metabolism, or a combination thereof, in the subject.

3. The method of claim 1, wherein the subject is a human aged 60 years or older.

4. The method of claim 1, wherein the muscular atrophy is non-inherited.

5. The method of claim 1, wherein the muscular atrophy is caused by aging, long-term bed rest, an assistive device for therapy, or cachexia.

6. The method of claim 1, wherein the muscular atrophy is not related to a deletion or a mutation of Survival Motor Neuron (SMN) gene.

7. A method of converting muscle type II into muscle type I, increasing muscle type I, strengthening muscles, or increasing the exercise performance in a subject with low expression of PGC-1α, the method comprising administering an effective amount of indoprofen, a pharmaceutically acceptable salt thereof, or a solvate thereof to the subject, thereby increasing expression of PGC-1α in the subject.

8. The method of claim 1, wherein the disease is muscular atrophy.

9. The method of claim 1, wherein the disease is obesity.

10. A method of increasing PGC-1α expression in a muscle cell in vitro, the method comprising administering an effective amount of indoprofen, a pharmaceutically acceptable salt thereof, or a solvate thereof to the cell, wherein the muscle cell is characterized by low expression of PGC-1α.

11. The method of claim 1 further comprising determining that the subject has low expression of PGC-1α prior to the administration of indoprofen.

* * * * *